(12) United States Patent
Choi et al.

(10) Patent No.: US 11,576,654 B2
(45) Date of Patent: Feb. 14, 2023

(54) ULTRASOUND DIAGNOSIS APPARATUS FOR MEASURING AND DISPLAYING ELASTICITY OF OBJECT AND METHOD OF OPERATING THE SAME

(71) Applicant: SAMSUNG MEDISON CO., LTD., Hongcheon-gun (KR)

(72) Inventors: Kiwan Choi, Seongnam-si (KR); Jiyoung Park, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 451 days.

(21) Appl. No.: 16/228,898

(22) Filed: Dec. 21, 2018

(65) Prior Publication Data
US 2019/0192120 A1    Jun. 27, 2019

Related U.S. Application Data

(60) Provisional application No. 62/608,863, filed on Dec. 21, 2017.

(30) Foreign Application Priority Data

Mar. 15, 2018  (KR) .................. 10-2018-0030413

(51) Int. Cl.
  *A61B 8/08*    (2006.01)
  *A61B 8/00*    (2006.01)

(52) U.S. Cl.
  CPC .............. *A61B 8/485* (2013.01); *A61B 8/463* (2013.01); *A61B 8/467* (2013.01); *A61B 8/5207* (2013.01); *A61B 8/5223* (2013.01); *A61B 8/54* (2013.01); *A61B 8/4405* (2013.01)

(58) Field of Classification Search
  CPC .......... A61B 8/485; A61B 8/463; A61B 8/467
  See application file for complete search history.

(56) References Cited

U.S. PATENT DOCUMENTS

| | | | |
|---|---|---|---|
| 2010/0016718 A1* | 1/2010 | Fan | G01S 7/52042 600/438 |
| 2012/0123263 A1 | 5/2012 | Osaka et al. | |
| 2012/0269416 A1* | 10/2012 | Waki | G01S 7/52063 382/131 |
| 2013/0317362 A1 | 11/2013 | Shi et al. | |
| 2014/0058259 A1 | 2/2014 | Liu | |

(Continued)

FOREIGN PATENT DOCUMENTS

| | | |
|---|---|---|
| CN | 105877783 A | 8/2016 |
| JP | 2015-128554 A | 7/2015 |

(Continued)

*Primary Examiner* — Joel Lamprecht
*Assistant Examiner* — Nyrobi Celestine
(74) *Attorney, Agent, or Firm* — Sughrue Mion, PLLC

(57) ABSTRACT

Provided are a method and ultrasound diagnosis apparatus for measuring and displaying an elasticity of an object. The ultrasound diagnosis apparatus includes: a processor configured to obtain elasticity data of a measurement target region of an object, calculate elasticity values of a plurality of regions included in the measurement target region based on the elasticity data by using different calculating methods, and combine the calculated elasticity values of the plurality of regions to calculate a final elasticity value; and a display configured to display the final elasticity value.

12 Claims, 12 Drawing Sheets

(56) References Cited

U.S. PATENT DOCUMENTS

| | | | |
|---|---|---|---|
| 2016/0183926 A1* | 6/2016 | Asami | A61B 8/5207 |
| | | | 600/438 |
| 2017/0112471 A1 | 4/2017 | Toji | |
| 2017/0311929 A1* | 11/2017 | Shao | G01S 7/52042 |
| 2017/0322308 A1 | 11/2017 | Loupas et al. | |
| 2017/0333004 A1* | 11/2017 | Yoshikawa | A61B 5/318 |
| 2017/0340310 A1* | 11/2017 | Carlini | A61B 8/485 |
| 2017/0347990 A1* | 12/2017 | Watanabe | G01S 15/8915 |
| 2017/0360408 A1* | 12/2017 | Toji | G01S 7/52017 |
| 2018/0025492 A1* | 1/2018 | Honjo | A61B 8/485 |
| | | | 382/128 |
| 2019/0046160 A1* | 2/2019 | Li | A61B 8/485 |
| 2020/0371232 A1* | 11/2020 | Loupas | G01S 15/8915 |

FOREIGN PATENT DOCUMENTS

| | | |
|---|---|---|
| JP | 2017-079977 A | 5/2017 |
| KR | 10-1646623 B1 | 8/2016 |
| KR | 10-2017-0085516 A | 7/2017 |
| WO | 2016/067072 A1 | 5/2016 |

\* cited by examiner

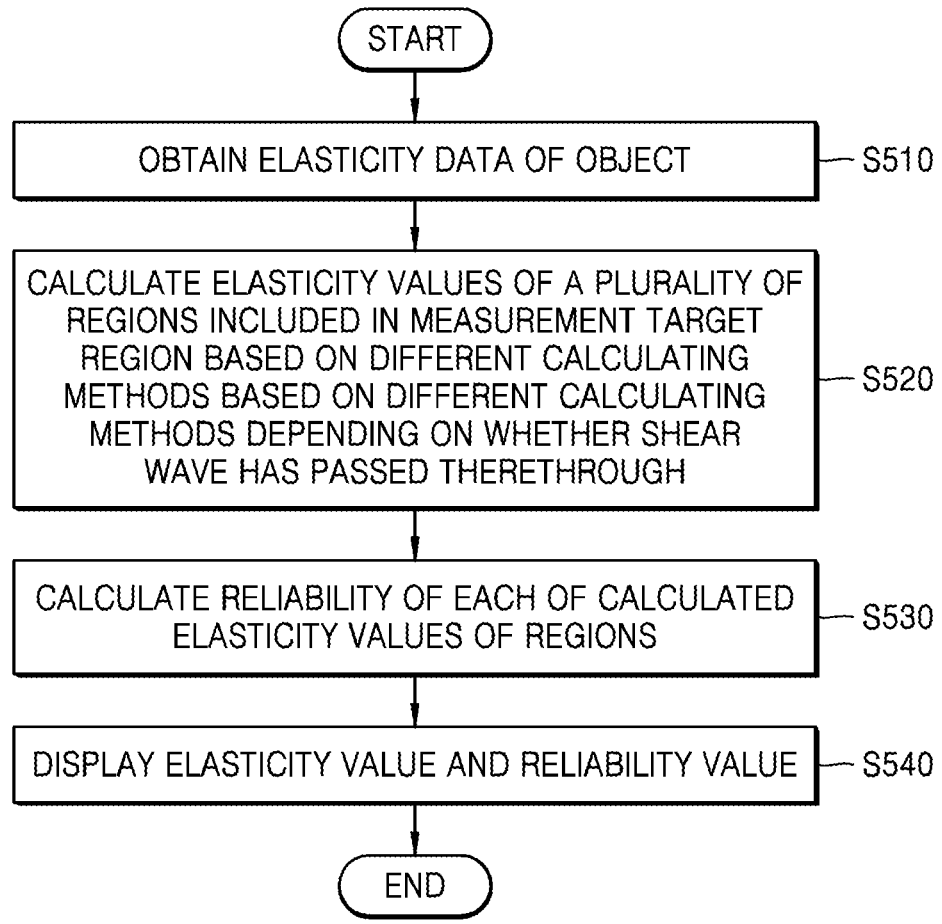
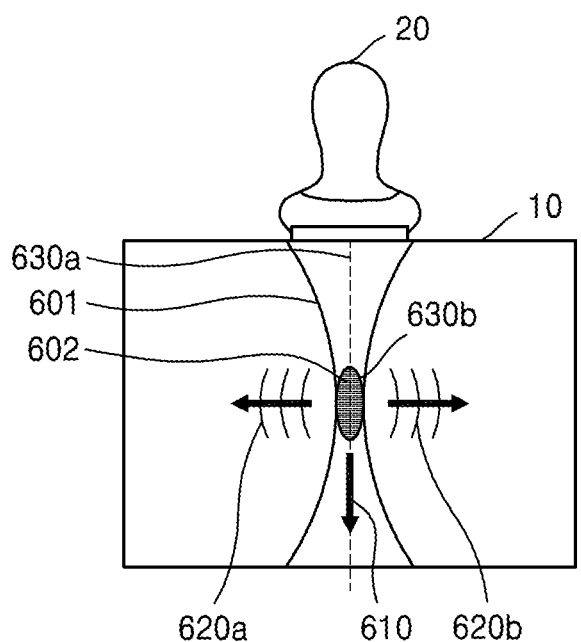

ULTRASOUND DIAGNOSIS APPARATUS FOR MEASURING AND DISPLAYING ELASTICITY OF OBJECT AND METHOD OF OPERATING THE SAME

CROSS-REFERENCE TO RELATED APPLICATION(S)

This application is based on and claims priority under 35 U.S.C. § 119 to U.S. Provisional Application No. 62/608,863, filed on Dec. 21, 2017, in the US Patent and Trademark Office and to Korean Patent Application No. 10-2018-0030413, filed on Mar. 15, 2018, in the Korean Intellectual Property Office, the disclosures of which are incorporated by reference herein in their entirety.

BACKGROUND

1. Field

The disclosure relates to methods and ultrasound imaging apparatuses (hereinafter, ultrasound image apparatuses are also referred to as ultrasound diagnosis apparatuses) for measuring and displaying an elasticity value of an object, and more particularly, to methods and apparatuses for measuring an elasticity value of an object in various ways by using an ultrasound wave.

2. Description of Related Art

Ultrasound diagnosis apparatuses transmit ultrasound signals generated by transducers of a probe to an object and receive information of signals reflected from the object, thereby obtaining at least one image of an internal part (e.g., soft tissues or blood flow) of the object. In particular, ultrasound diagnosis apparatuses are used for medical purposes including observing an internal area of an object, detecting foreign substances, and assessing injuries. Such ultrasound diagnosis apparatuses exhibit high stability, display images in real-time, and are safe due to lack of radiation exposure, compared to diagnostic X-ray apparatuses. Therefore, ultrasound diagnosis apparatuses have been widely used together with other types of imaging diagnosis apparatuses including a computed tomography (CT) apparatus and a magnetic resonance imaging (MRI) apparatus.

SUMMARY

Provided are methods and apparatuses for precisely measuring and providing elasticity of an object. More specifically, provided are methods and apparatuses for calculating elasticities of a plurality of regions included in a measurement target region, based on various calculating methods.

Additional aspects will be set forth in part in the description which follows and, in part, will be apparent from the description, or may be learned by practice of the presented embodiments.

In accordance with an aspect of the disclosure, an ultrasound diagnosis apparatus includes: a processor configured to obtain elasticity data of a measurement target region of an object, calculate elasticity values of a plurality of regions included in the measurement target region based on the elasticity data by using different calculating methods, and combine the calculated elasticity values of the plurality of regions to calculate a final elasticity value; and a display configured to display the final elasticity value.

The processor may be further configured to determine an initially detected location of a shear wave displacement, and determine whether a shear wave has passed through each of the plurality of regions by comparing the initially detected location of the shear wave displacement with a location of each of the plurality of regions.

The processor may be further configured to set a reference value based on a distance between the initially detected location of the shear wave displacement and a focus beam irradiation line, set a distance value of each region based on an average distance between each region included in the plurality of regions and the focus beam irradiation line, and determine whether a shear wave has passed through each region by comparing the reference value with the distance value.

The processor may be further configured to determine a method of calculating an elasticity value of a region determined as a shear wave-pass-region among the plurality of regions as a first calculating method, and determine a method of calculating an elasticity value of a region determined as a shear wave-non-pass-region as a second calculating method, the first calculating method being a method of predicting and calculating the elasticity value of the region determined as the shear wave-pass-region based on the elasticity data.

The first calculating method may calculate a shear wave average velocity in the shear wave-pass-region by using the initially detected location of the shear wave displacement, and predict and calculate an elasticity value based on the shear wave average velocity.

The processor may be further configured to calculate reliability of the calculated elasticity values of the plurality of regions based on a determined method of calculating an elasticity value, and the display may further display the reliability.

The processor may be further configured to calculate an elasticity value of a region determined as a shear wave-pass-region among the plurality of regions by using a first calculating method, calculate an elasticity value of a region determined as a shear wave-non-pass region by using a second calculating method, and set reliability of the elasticity value calculated based on the first calculating method to a preset reliability value.

The processor may be further configured to control the display to selectively display only a portion of the final elasticity value based on the reliability.

The ultrasound diagnosis apparatus may further include an input interface configured to receive a user input, and the processor may control the display to select only a portion of the final elasticity value based on the user input, and display the selected final elasticity value and an elasticity value calculating method of the selected final elasticity value.

In accordance with another aspect of the disclosure, a method of operating an ultrasound diagnosis apparatus includes: obtaining elasticity data of a measurement target region of an object; calculating elasticity values of a plurality of regions included in the measurement target region based on the elasticity data by using different calculating methods; combining the calculated elasticity values of the plurality of regions to calculate a final elasticity value; and displaying the final elasticity value.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 5 is a flowchart for explaining a method, performed by an ultrasound diagnosis apparatus, of displaying an elasticity value and reliability of an object, according to an embodiment;

FIGS. 6A and 6B are views for explaining a process of generating a shear wave irradiated to an object, by an ultrasound diagnosis apparatus, according to an embodiment;

DETAILED DESCRIPTION

Figure 1:
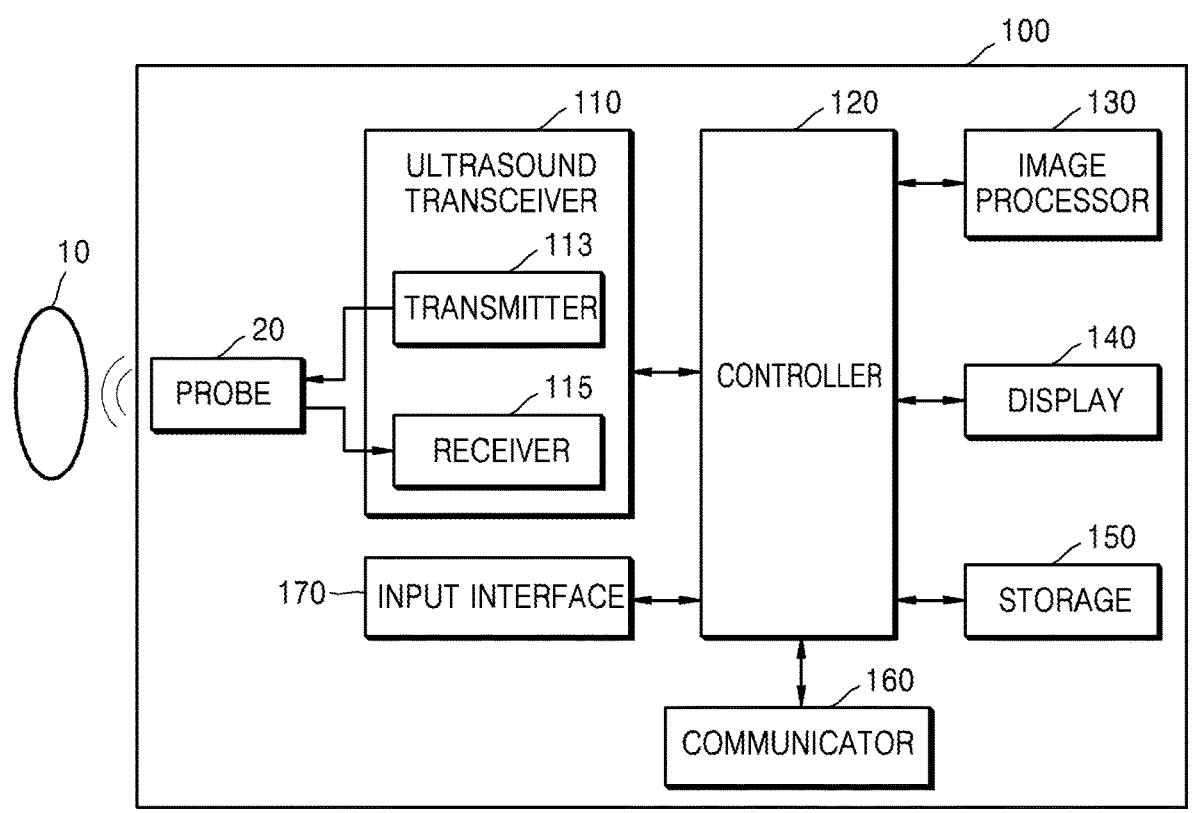
FIG. 1 is a block diagram illustrating an ultrasound diagnosis apparatus according to an exemplary embodiment.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

Like reference numerals refer to like elements throughout. The present specification does not describe all components in the embodiments, and common knowledge in the art or the same descriptions of the embodiments will be omitted below. The term "part" or "portion" used herein may be implemented using hardware or software, and according to embodiments, a plurality of "parts" or "portions" may be formed as a single unit or element, or one "part" or "portion" may include a plurality of units or elements. Expressions such as "at least one of," when preceding a list of elements, modify the entire list of elements and do not modify the individual elements of the list. Hereinafter, the operating principles and embodiments of the disclosure will be described in detail with reference to the accompanying drawings.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked by wire or wirelessly. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include instruction languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

FIGS. 2A, 2B, and 2C are diagrams illustrating ultrasound diagnosis apparatus according to an exemplary embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUI), thereby receiving user's inputs of data to control the ultrasound diagnosis apparatus 100. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100 may control the display of the ultrasound image on the main display 121 by using the input control data.

Figure 2:
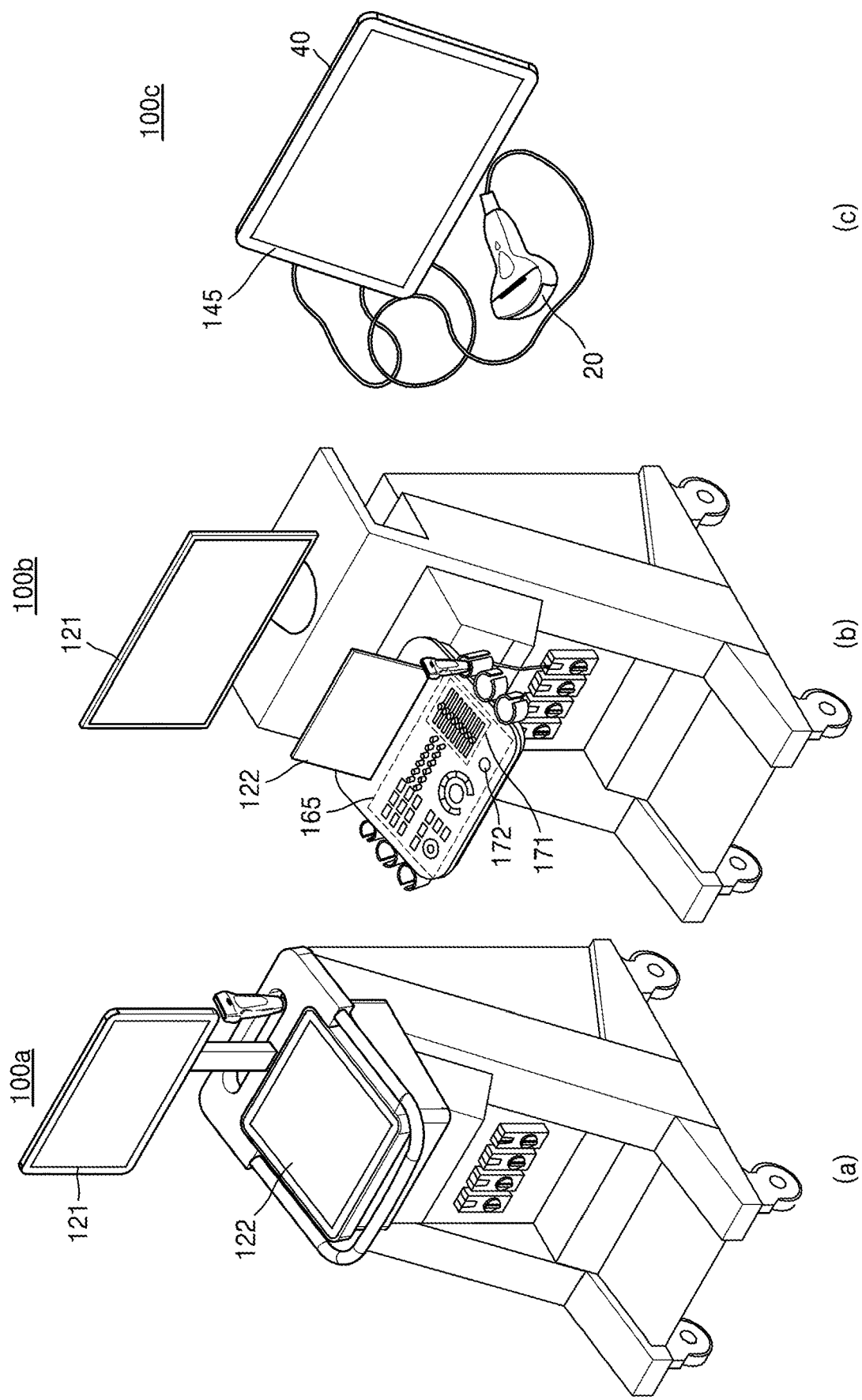
FIG. 2 is a diagram respectively illustrating an ultrasound diagnosis apparatus according to an exemplary embodiment.

Referring to FIG. 2, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected while scanning an ultrasound image, the ultrasound diagnosis apparatus 100 may keep displaying a frame image at that time point.

The buttons, trackballs, jog switches, and knobs included in the control panel 165 may be provided as a GUI to the main display 121 or the sub-display 122.

Referring to FIG. 2, the ultrasound diagnosis apparatus 100 may include a portable device. An example of the portable-type ultrasound diagnosis apparatus 100 may include, for example, smart phones including probes and applications, laptop computers, personal digital assistants (PDAs), or tablet PCs, but an exemplary embodiment is not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

Figure 3:
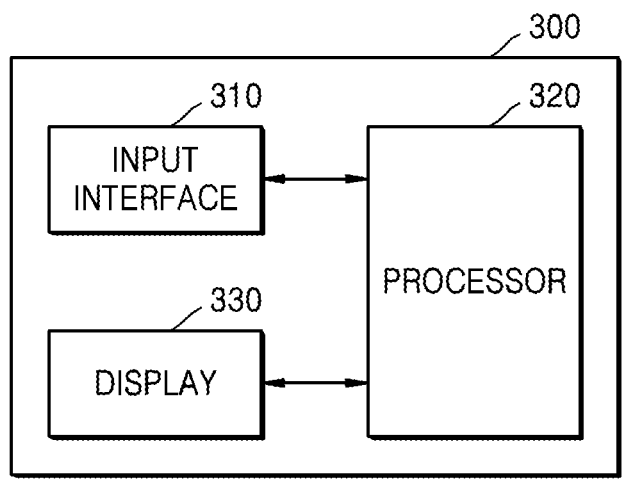
FIG. 3 is a block diagram of a configuration of an ultrasound diagnosis apparatus according to an embodiment.

FIG. 3 is a block diagram of a configuration of an ultrasound diagnosis apparatus 300 according to an embodiment.

The ultrasound diagnosis apparatus 300 according to an embodiment includes an input interface 310, a processor 320, and a display 330. In an embodiment, the ultrasound diagnosis apparatus 300 may include the number of elements less than the number of elements shown in FIG. 3, or may further include additional elements. For example, the ultrasound diagnosis apparatus 300 may receive a user input from a separate device instead of including the input interface 310.

The processor 320 according to an embodiment may obtain elasticity data of an object. Also, the processor 320 may obtain a measurement value from elasticity data. The measurement value may denote a value which may be obtained from elasticity data such as a velocity of a measured shear wave, an elasticity value, reliability of an elasticity value, and a standard deviation of an elasticity value.

A method of obtaining an elasticity value of an object at the processor 320 may be implemented variously depending on an embodiment. For example, when a user sets a region of interest (ROI) in an ultrasound image, the ultrasound diagnosis apparatus 300 may irradiate an ultrasound signal for pushing a partial region of an object to the object by using the ultrasound transceiver 110 and the probe 20 of FIG. 1.

The processor 320 may determine a focus beam irradiation line for determining an irradiation location of an ultrasound wave. The processor 320 may irradiate an ultrasound signal to a shear wave induction location on the determined focus beam irradiation line. The ultrasound diagnosis apparatus 300 may obtain an elasticity value by tracing a shear wave (also referred to as a shear wave) induced by the irradiated ultrasound signal.

In an embodiment, an ultrasound signal for inducing a shear wave may be an acoustic radiation force impulse (ARFI). When a shear wave is induced to a tissue inside an object by an ARFI, a shear wave displacement may occur. The processor 320 may trace a shear wave by measuring a shear wave displacement of an object, and calculate an elasticity value of the object based on this. However, the technical spirit of obtaining an elasticity value is not limited to the above example.

The processor 320 may calculate an elasticity value of a plurality of regions included in a measurement target region based on different calculating methods. In an embodiment, while initially detecting a shear wave displacement, the processor 320 may calculate an elasticity value based on a first calculating method with respect to a region through which a shear wave has passed and calculate an elasticity value based on a second calculating method with respect to a region through which a shear wave has not passed.

In the case of inducing a shear wave to a tissue by using an ultrasound signal, a velocity of the induced shear wave changes based on an elasticity value of the tissue region to which the shear wave has been induced. For example, when a shear wave is induced into a solid tissue having a large elasticity value, the shear wave is transferred at a very fast velocity. In this case, a region through which a shear wave passes before a shear wave displacement is detected, may occur in a measurement target region of an object. Calculation of an elasticity value by using a shear wave displacement may be difficult with respect to this shear wave-pass-region.

In an embodiment, the first calculating method may calculate an average velocity of a shear wave in a region through which the shear wave has passed by using an initially detected location of a shear wave displacement, and calculate an elasticity value of a shear wave-pass-region based on this. An average velocity of a shear wave may be calculated by using a time taken from inducing the shear wave to detecting a shear wave displacement, and a distance from a focus beam irradiation line to the initially detected location of the shear wave displacement. However, a method of predicting and calculating an elasticity value of a shear wave-pass-region is not limited to the above example.

In an embodiment, the processor 320 may calculate an elasticity value of a region in which an average distance between the region and a focus beam irradiation line is less than a reference value based on the first calculating method, and calculate an elasticity value of a region in which an average distance between the region and the focus beam irradiation line is equal to or greater than the reference value based on the second calculating method. The reference value may be determined based on the initially detected location of the shear wave displacement. In this case, the region in which an average distance between the region and the focus beam irradiation line is less than the reference value may be a region through which a shear wave has passed before a shear wave initial detected time.

The processor 320 may calculate a reliability value of an elasticity value calculated for each region. For example, the processor 320 may calculate a reliability value of an elasticity value based on a magnitude of a detected shear wave to obtain the elasticity value. That is, the processor 320 may determine that reliability of an elasticity value is high when a magnitude of a shear wave is large, and reliability of an elasticity value is low when a magnitude of a shear wave is small. However, it is not limited thereto. For example, the processor 320 may determine reliability of an elasticity value by using a residual value as well as a magnitude of a shear wave. That is, the processor 320 may determine that reliability of an elasticity value is high when a residual value is small, and reliability of an elasticity value is low when a residual value is large.

Meanwhile, the processor 320 may give a preset reliability value to an elasticity value. For example, the processor 320 may give a preset low reliability value to an elasticity value calculated based on a calculating method having low accuracy.

The processor 320 may give different reliability values depending on a method of calculating an elasticity value. For example, the processor 320 may give a preset reliability value to an elasticity value calculated based on the first calculating method, and give a reliability value calculated based on a shear wave to an elasticity value calculated based on the second calculating method. The preset reliability value may be a value less than an average of reliability values calculated based on a shear wave. However, a technical spirit of giving different reliability values depending on a method of calculating an elasticity value is not limited thereto.

Meanwhile, since the ultrasound diagnosis apparatus 300 performs a process of obtaining an elasticity value of an object plurality of number of times, the processor 320 may calculate a plurality of elasticity values of respective regions included in a measurement target region of an object. Since a shear wave induction location may change depending on a process, a plurality of elasticity values of the same region calculated a plurality of number of times of processes may be elasticity values calculated based on different calculating methods.

The processor 320 may select some of a plurality of elasticity values calculated for the same region. For example, the processor 320 may select an elasticity value having a high reliability value among the plurality of elasticity values.

The processor 320 may combine elasticity values calculated for respective regions. For example, the processor 320 may generate information representing an elasticity value of an entire measurement target region. In an embodiment, the processor 320 may combine elasticity values based on a reliability value of the calculated elasticity values.

The processor 320 may include hardware units including a memory and a processor, the memory storing at least one of a program, an algorithm, and application data for calculating elasticity values of a plurality of regions included in a measurement target region based on different calculating methods, the processor processing the program, the algorithm, or the application data stored in the memory. For example, the processor 320 may include a processor including at least one of a central processing unit, a microprocessor, and a graphic processing unit. In this case, the memory and the processor may be configured as a single chip and are not limited thereto.

The display 330 may display the information generated by the processor 320. The information displayed by the display 330 may change variously depending on an embodiment. For example, the display 330 may display a graph showing an elasticity value by using a dot, a line, or a rod. Also, the display 330 may further display a reliability value of an elasticity value. In addition, the display 330 may further display information about a method of calculating an elasticity value. For example, the display 330 may display information showing that a currently displayed elasticity value is an elasticity value calculated by using the first calculating method.

The display 330 may selectively display only some of elasticity values. For example, the display 330 may display an elasticity value calculated based on the second calculating method and may not display an elasticity value calculated based on the first calculating method. Or the display 330 may not display an elasticity value having a reliability value less than a reference value based on the reliability value. The processor 320 may control a selective displaying operation of the display 330 in response to an input from outside.

Figure 4:
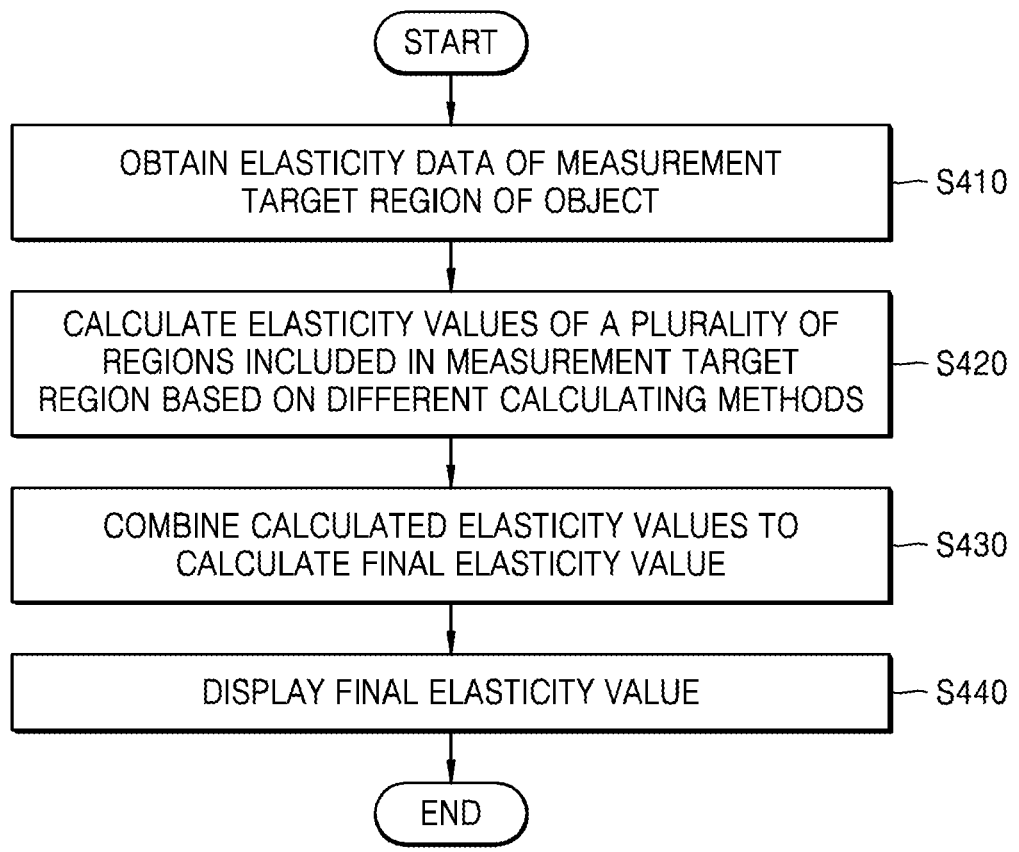
FIG. 4 is a flowchart for explaining a method, performed by an ultrasound diagnosis apparatus, of displaying an elasticity value of an object, according to an embodiment.

FIG. 4 is a flowchart for explaining a method, performed by an ultrasound diagnosis apparatus, of displaying an elasticity value of an object, according to an embodiment.

In operation S410, the ultrasound diagnosis apparatus obtains elasticity data of a measurement target region of an object. In an embodiment, the ultrasound diagnosis apparatus may cause a displacement of a tissue by applying an ultrasound signal into a body, which is an object to examine, by using an ultrasound probe. When a shear wave is induced to the tissue inside the object by the ultrasound signal, a displacement of the tissue may be generated. The ultrasound diagnosis apparatus may obtain elasticity data of the object by detecting a shear wave displacement due to the induced shear wave.

In operation S420, the ultrasound diagnosis apparatus calculates elasticity values of a plurality of regions included in the measurement target region by using different calculating methods based on the elasticity data.

In an embodiment, the ultrasound diagnosis apparatus may divide a plurality of regions included in the measurement target region based on whether a shear wave has passed through a relevant region while a shear wave displacement is initially detected. The ultrasound diagnosis apparatus may determine a method of calculating an elasticity value of the relevant region based on a division result. For example, the ultrasound diagnosis apparatus may calculate an elasticity value based on the first calculating method with respect to a shear wave-pass region, and calculate an elasticity value based on the second calculating method with respect to a shear wave-non-pass region.

In an embodiment, the first calculating method may calculate an average velocity of a shear wave in a region through which a shear wave has passed by using an initially detected location of a shear wave displacement, and calculate an elasticity value of the shear wave-pass-region based on this. An average velocity of a shear wave may be calculated by using a time taken from inducing the shear wave to detecting a shear wave displacement, and a distance from a focus beam irradiation line to the initially detected location of the shear wave displacement. However, a method of predicting and calculating an elasticity value of a shear wave-pass-region is not limited to the above example.

In an embodiment, the ultrasound diagnosis apparatus may calculate an elasticity value of a region in which an average distance between the region and the focus beam irradiation line is less than a reference value based on the first calculating method, and calculate an elasticity value of a region in which an average distance between the region and the focus beam irradiation line is equal to or greater than the reference value based on the second calculating method. The reference value may be determined based on the initially detected location of the shear wave displacement. In this case, the region in which an average distance between the region and the focus beam irradiation line is less than the reference value may be a region through which a shear wave has passed before a shear wave initial detected time.

In operation S430, the ultrasound diagnosis apparatus calculates a final elasticity value by combining the calculated elasticity values. For example, the final elasticity value may be information representing an elasticity value of the entire measurement target region. Alternatively, the final elasticity value may be information including only elasticity values calculated based on selected some calculating methods. However, a technical spirit of calculating a final elasticity value by combining the calculated elasticity values is not limited thereto.

In operation S440, the ultrasound diagnosis apparatus displays a final elasticity value. The ultrasound diagnosis apparatus may display an elasticity value in various forms by using a graphic user interface.

The ultrasound diagnosis apparatus may selectively display only some of elasticity values. For example, the ultrasound diagnosis apparatus may display elasticity values calculated based on the second calculating method and may not display elasticity values calculated based on the first calculating method depending on methods of calculating an elasticity value.

FIG. 5 is a flowchart for explaining a method, performed by an ultrasound diagnosis apparatus, of displaying an elasticity value and a reliability value of an object, according to an embodiment. The ultrasound diagnosis apparatus of FIG. 5 calculates a reliability value of an elasticity value and displays the reliability value and the elasticity value together.

In operation S510, the ultrasound diagnosis apparatus obtains elasticity data of an object. A method in which the ultrasound diagnosis apparatus obtains the elasticity data of the object is described in detail with reference to FIG. 4.

In operation S520, the ultrasound diagnosis apparatus calculates elasticity values of a plurality of regions included in a measurement target region based on different calculating methods. A method in which the ultrasound diagnosis apparatus calculates the elasticity values of the plurality of regions included in the measurement target region is described in detail with reference to FIG. 4.

In operation S530, the ultrasound diagnosis apparatus calculates reliability of a calculated elasticity value of each region. For example, the ultrasound diagnosis apparatus may calculate a reliability value of an elasticity value based on a detected magnitude of a shear wave in order to obtain the elasticity value of each region. That is, the ultrasound diagnosis apparatus may determine that reliability of an elasticity value is high when a magnitude of a shear wave is large, and reliability of an elasticity value is low when a magnitude of a shear wave is small. The ultrasound diagnosis apparatus may use a wave equation in calculating reliability of an elasticity value. However, a technical spirit of calculating reliability of a calculated elasticity value is not limited thereto.

Meanwhile, the ultrasound diagnosis apparatus may give a preset reliability value to an elasticity value. For example, the ultrasound diagnosis apparatus may give a preset low reliability value to an elasticity value calculated based on a calculating method of a low accuracy.

The ultrasound diagnosis apparatus may give different reliability values depending on a method of calculating an elasticity value. For example, the ultrasound diagnosis apparatus may give a preset reliability value to an elasticity value calculated based on the first calculating method, and give a reliability value calculated based on a shear wave to an elasticity value calculated based on the second calculating method. The preset reliability value may be a value less than an average of reliability values calculated based on a shear wave. However, a technical spirit of giving different reliability values depending on a method of calculating an elasticity value is not limited to the above example.

Meanwhile, the ultrasound diagnosis apparatus may calculate a plurality of elasticity values of respective regions included in a measurement target region of an object by performing a process of obtaining an elasticity value of the object plurality of number of times. Since a shear wave induction location may change depending on a process, a plurality of elasticity values of the same region calculated a plurality of number of times of processes may be elasticity values calculated based on different calculating methods.

The ultrasound diagnosis apparatus may select some of a plurality of elasticity values of the same region. For example, the ultrasound diagnosis apparatus may select an elasticity value having a highest reliability value among the plurality of elasticity values of the same region.

The ultrasound diagnosis apparatus may combine elasticity values calculated for respective regions. For example, the ultrasound diagnosis apparatus may generate information representing an elasticity value of the entire measurement target region. In an embodiment, the ultrasound diagnosis apparatus may combine elasticity values based on reliability values of the calculated elasticity values.

In operation S540, the ultrasound diagnosis apparatus displays an elasticity value and a reliability value. The ultrasound diagnosis apparatus may display an elasticity value and a reliability value thereof in various forms by using a graphic user interface. For example, the ultrasound diagnosis apparatus may display a reliability value in various forms such as letters, graphs, etc.

In addition, the ultrasound diagnosis apparatus may further display information about a method of calculating an elasticity value. For example, the ultrasound diagnosis apparatus may display information that a currently displayed elasticity value is an elasticity value calculated based on the first calculating method. In an embodiment, the ultrasound diagnosis apparatus may display warning information that an elasticity value calculated based on the first calculating method has reliability less than that of an elasticity value calculated based on the second calculating method.

The ultrasound diagnosis apparatus may selectively display only some of elasticity values. For example, the ultrasound diagnosis apparatus may display an elasticity value calculated based on the second calculating method and may not display an elasticity value calculated based on the first calculating method depending on a method of calculating an elasticity value. Alternatively, the ultrasound diagnosis apparatus may not display an elasticity value having a reliability value less than a reference value based on the reliability value.

In an embodiment, the ultrasound diagnosis apparatus may include a user input interface configured to receive a user input. The user input interface may include a hardware configuration, for example, a keypad, a mouse, a track ball, a touchpad, a touchscreen, a jog switch, etc. and is not limited thereto. In an embodiment, the user input interface may receive a user input that sets a display environment to selectively display only some of elasticity values. The ultrasound diagnosis apparatus may display only some selected from elasticity values based on a received user input.

Figure 6B:
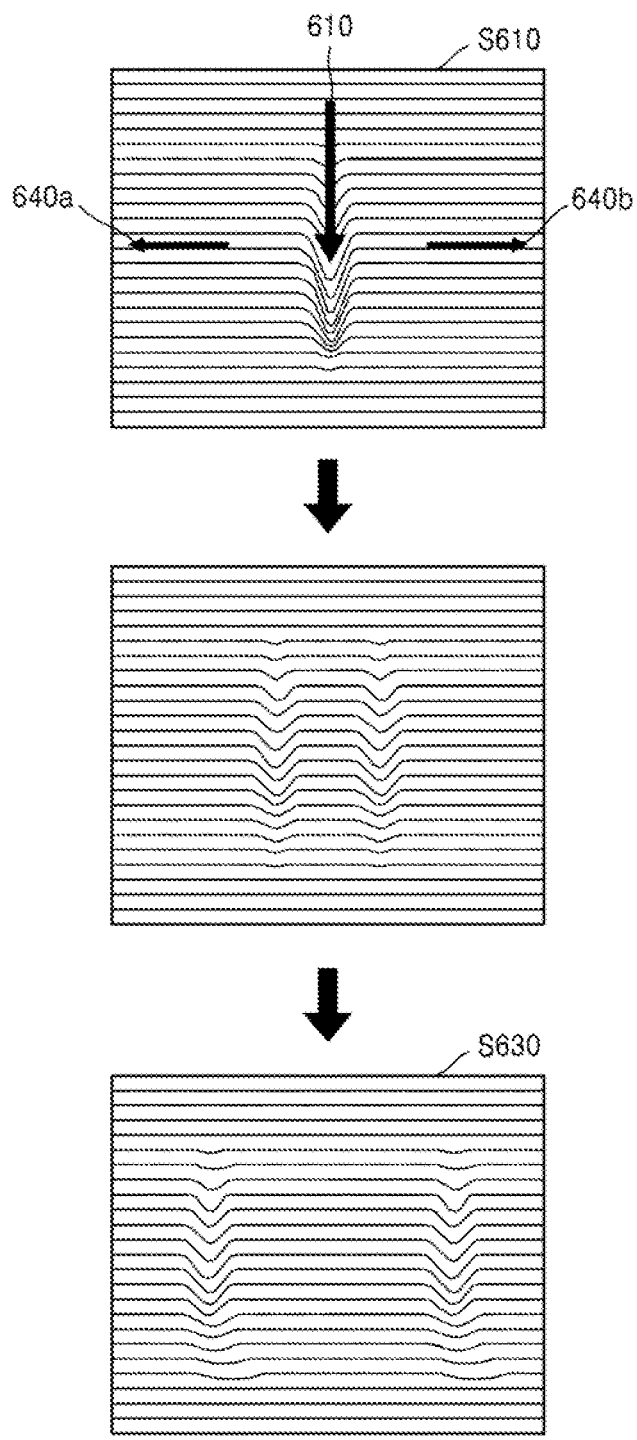

FIGS. 6A and 6B are views for explaining a process of generating a shear wave irradiated to an object, by an ultrasound diagnosis apparatus, according to an embodiment.

Referring to FIG. 6A, the probe 20 may induce a displacement 610 of the object 10 by irradiating a focus beam 601, which is an ultrasound signal, to the object 10. When the focus beam 601 is irradiated to the object 10, the displacement 610 of the object 10 is induced at a shear wave induced location 602 at which the focus beam 601 is focused. Due to the displacement 610 of the object 10, shear waves 620a and 620b (also referred to as shear waves) propagating in a direction perpendicular to the displacement 610 are generated from a point at which the displacement 610 has occurred. The shear waves generated from the shear wave induced location 602 propagate in the direction perpendicular to the displacement 610 and gradually weaken and vanish. A mode in which the shear wave of the object 10 is captured is called a shear wave elasticity mode. The shear wave elasticity mode may include a two-dimensional (2D) shear wave measurement mode and a point shear wave measurement mode, and the scope of the present disclosure is not limited thereto.

In an embodiment illustrated in FIG. 6A, the ultrasound diagnosis apparatus may generate a shear wave to an object by irradiating a focus beam to a shear wave induction location 630b on a determined focus beam irradiation line 630a.

FIG. 6B is a view for explaining propagation of a shear wave. In an embodiment, a shear wave generated by the probe 20 may induce the displacement 610 at a focused location, and propagate in directions 640a and 640b as shown in S610 and S630.

Figure 7A:
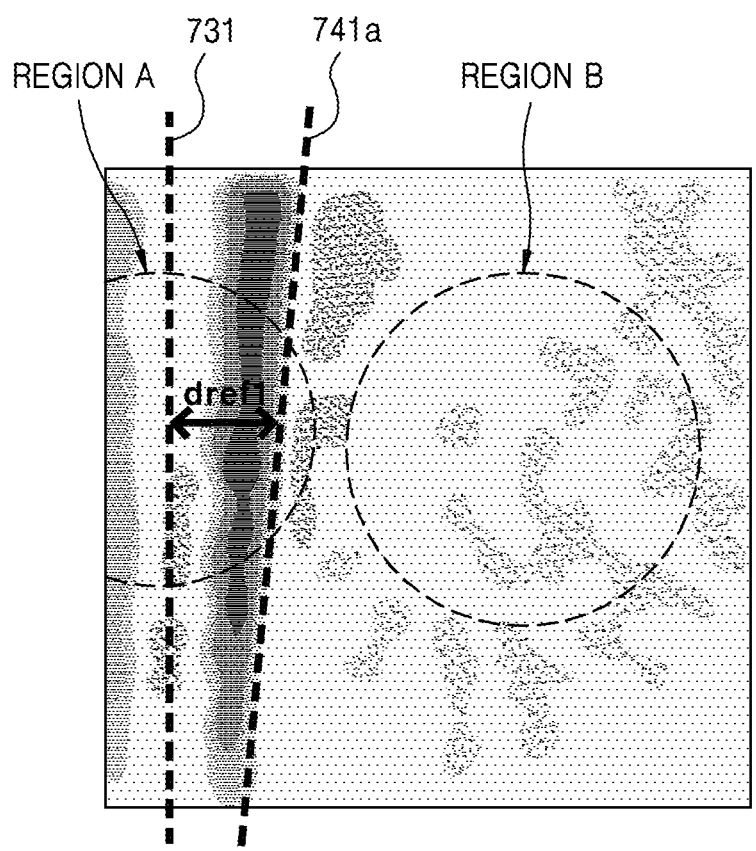
FIGS. 7A and 7B are views for explaining a method, performed by an ultrasound diagnosis apparatus, of detecting a displacement of a shear wave, according to an embodiment.
Figure 7B:
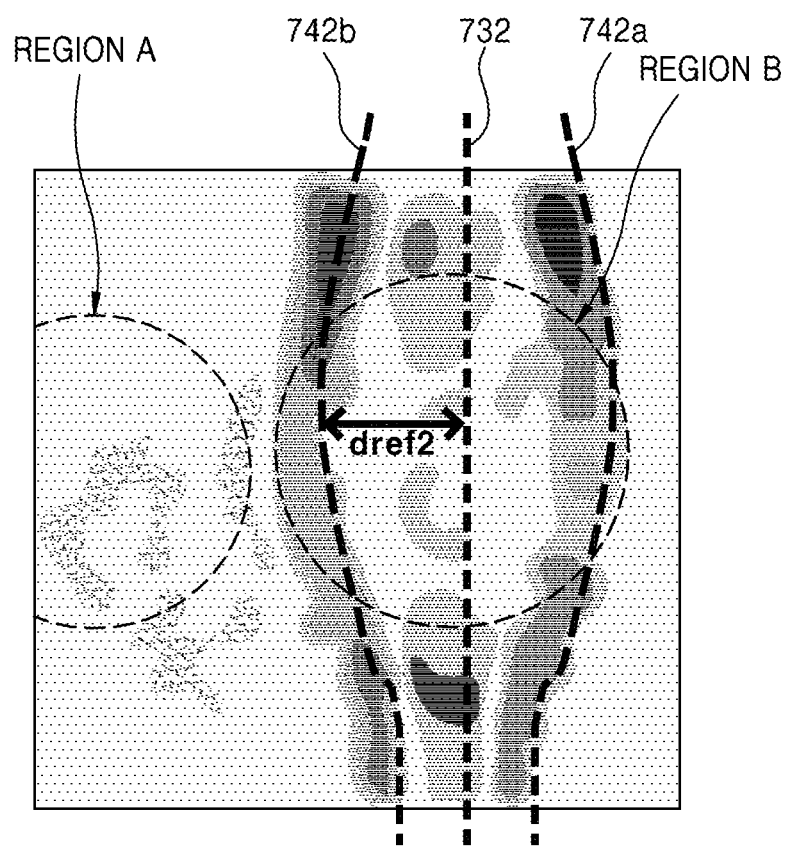

FIGS. 7A and 7B are views for explaining a method, performed by an ultrasound diagnosis apparatus, of detecting a displacement of a shear wave, according to an embodiment.

FIG. 7A illustrates results obtained while a displacement of an object due to an induced shear wave is observed when an ultrasound signal is irradiated to a region A. Referring to FIG. 6A, the ultrasound diagnosis apparatus may irradiate an ultrasound signal to an object in a focus beam irradiation line 731. A shear wave induced due to an ultrasound signal propagates in a direction perpendicular to the focus beam irradiation line 731.

An initially detected location 741a of a shear wave displacement is determined based on a point at which a shear wave has arrived when a shear wave has been initially observed. Meanwhile, the point at which the shear wave has arrived when the shear wave has been initially observed is determined based on a velocity of the shear wave, and the velocity of the shear wave is determined based on an elasticity value of a region through which the shear wave has passed while the shear wave propagates. For example, a velocity of a shear wave gets fast when the shear wave passes through a region having a large elasticity value, that is, a solid region. Since an elasticity value of an object changes depending on a region, the initially detected location 741a of the shear wave displacement changes depending on a value of a z-axis.

The ultrasound diagnosis apparatus may determine a distance between the initially detected location 741a of the shear wave displacement and the focus beam irradiation line 731 as a reference value dref1. As described above, the reference value dref1 may change depending on a value of the z-axis.

FIG. 7B illustrates a result obtained by observing a displacement of an object due to an induced shear wave when an ultrasound signal is irradiated to a region B. Referring to FIG. 7B, the ultrasound diagnosis apparatus may irradiate an ultrasound signal to an object in a direction of a focus beam irradiation line 732. A shear wave induced due to an ultrasound signal propagates in a direction perpendicular to the focus beam irradiation line 732.

Initially detected locations 742a and 742b of a shear wave displacement are determined based on a point at which a shear wave has arrived when a shear wave has been initially observed. The ultrasound diagnosis apparatus may determine a distance between the initially detected locations 742a and 742b of the shear wave displacement, and a focus beam irradiation line 731 as a reference value dref2. As described above, the reference value dref2 may change depending on a value of the z-axis.

Since the reference value dref2 of the region B is greater than the reference value dref1 of the region A, the ultrasound diagnosis apparatus may determine that the region B is a solid region having a larger elasticity value than that of the region A.

Figure 8:
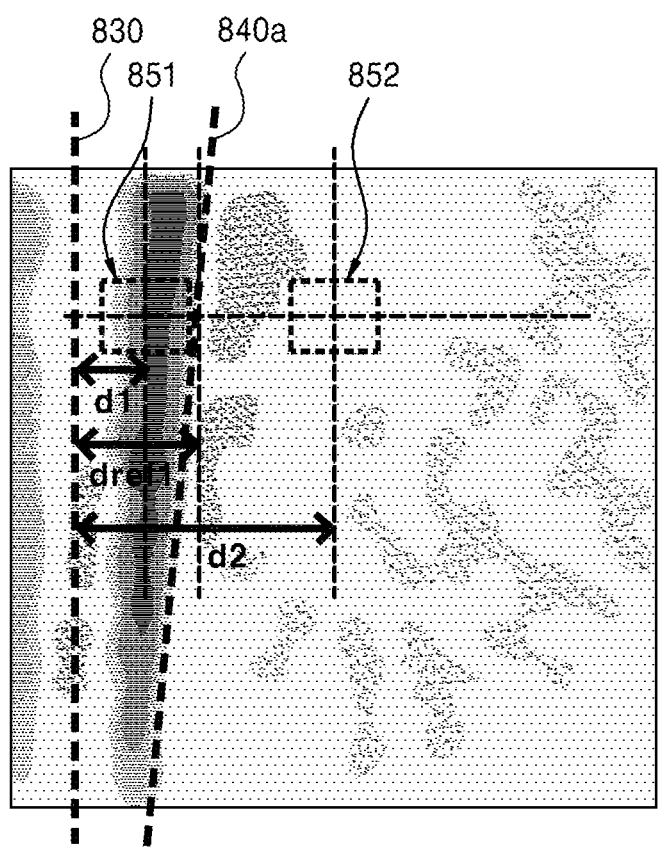
FIG. 8 is a view for explaining a method, performed by an ultrasound diagnosis apparatus, of determining a method of calculating an elasticity value of a specific region, according to an embodiment.

FIG. 8 is a view for explaining a method, performed by an ultrasound diagnosis apparatus, of determining a method of calculating an elasticity value of a specific region, according to an embodiment.

In an embodiment, the ultrasound diagnosis apparatus may divide a plurality of regions included in a measurement target region based on whether a shear wave has passed through a relevant region when a shear wave displacement is initially detected. The ultrasound diagnosis apparatus may determine a method of calculating an elasticity value of the relevant region based on the divided result.

Referring to FIG. 8, the ultrasound diagnosis apparatus may irradiate an ultrasound signal to an object in a direction of a focus beam irradiation line 830. A shear wave induced due to an ultrasound signal propagates in a direction perpendicular to the focus beam irradiation line 830. In an embodiment, the ultrasound diagnosis apparatus may determine a distance between an initially detected location 840a of a shear wave displacement and the focus beam irradiation line 830 as a reference value dref.

The ultrasound diagnosis apparatus may determine a method of calculating an elasticity value of a first region 851 based on whether a shear wave has passed through the first region 851 when a shear wave displacement is initially observed. In an embodiment, the ultrasound diagnosis apparatus may calculate a first distance d1, which is an average distance between the first region 851 and the focus beam irradiation line 830. The ultrasound diagnosis apparatus may determine whether a shear wave has passed through the first region 851 when the shear wave displacement is initially observed by comparing the first distance d1 with the reference value dref.

Likewise, the ultrasound diagnosis apparatus may determine a method of calculating an elasticity value of a second region 852 based on whether a shear wave has passed through the second region 852 when a shear wave displacement is initially observed. In an embodiment, the ultrasound diagnosis apparatus may calculate a second distance d2, which is an average distance between the second region 852 and the focus beam irradiation line 830. The ultrasound diagnosis apparatus may determine whether a shear wave has passed through the second region 852 when the shear wave displacement is initially observed by comparing the second distance d2 with the reference value dref.

The ultrasound diagnosis apparatus may determine that a region in which a distance to the focus beam irradiation line is less than the reference value is a region through which a shear wave has passed. For example, the ultrasound diagnosis apparatus may determine that the first region 851 is a shear wave-pass-region because the first distance d1 is less than the reference value dref. Also, the ultrasound diagnosis apparatus may determine that the second region 852 is a shear wave-non-pass region because the second distance d2 is greater than the reference value dref.

In an embodiment, the ultrasound diagnosis apparatus may calculate an elasticity value of a shear wave-pass-region based on the first calculating method, and calculate an elasticity value of a shear wave-non-pass-region based on the second calculating method. For example, the ultrasound diagnosis apparatus may calculate an elasticity value of a region in which an average distance between the region and the focus beam irradiation line is less than the reference value based on the first calculating method, and calculate an elasticity value of a region in which an average distance between the region and the focus beam irradiation line is greater than the reference value based on the second calculating method.

In an embodiment, the first calculating method may calculate an average velocity of a shear wave in a region through which a shear wave has passed by using an initially detected location of a shear wave displacement, and calculate an elasticity value of the shear wave-pass-region based on this. An average velocity of a shear wave may be calculated by using a time taken from inducing the shear wave to detecting a shear wave displacement, and a distance from a focus beam irradiation line to the initially detected location of the shear wave displacement. However, a method of predicting and calculating an elasticity value of a shear wave-pass-region is not limited to the above example.

FIGS. 9A to 9D are views for explaining a method, performed by an ultrasound diagnosis apparatus, of displaying an elasticity value, according to an embodiment.

Figure 9A:
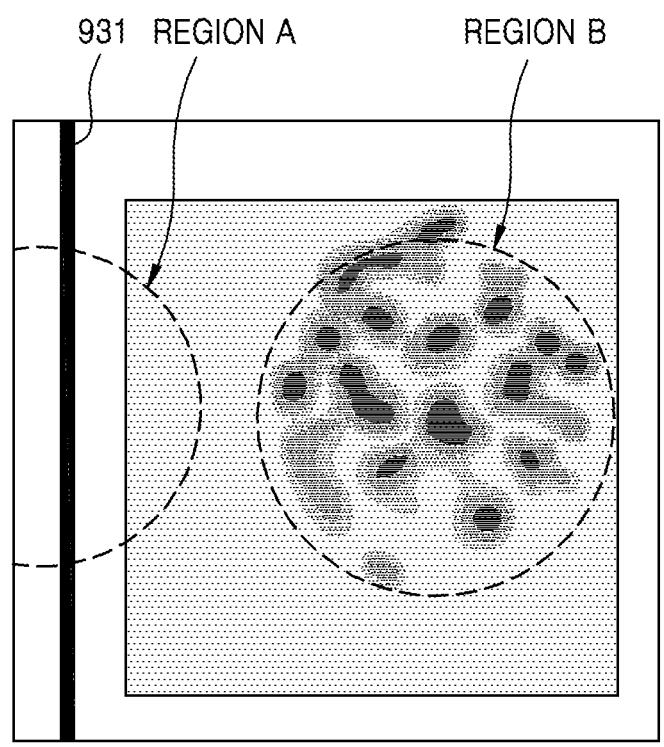
FIGS. 9A to 9D are views for explaining a method, performed by an ultrasound diagnosis apparatus, of displaying an elasticity value, according to an embodiment.

FIG. 9A illustrates a result of displaying elasticity values calculated based on a shear wave induced when the ultrasound diagnosis apparatus irradiates an ultrasound signal in a direction of a focus beam irradiation line 931. Reference values of REGION A and REGION B shown in FIGS. 9A to 9D are defined to be different. For example, as described above, the reference value dref2 of the region B is greater than the reference value dref1 of the region A.

The ultrasound diagnosis apparatus may divide a plurality of regions included in a measurement target region based on whether a shear wave has passed through a relevant region when a shear wave displacement is initially detected. Ultrasound diagnosis apparatus may determine a method of calculating an elasticity value of the relevant region based on a divided result.

In an embodiment, the ultrasound diagnosis apparatus may calculate an elasticity value of a transverse-pass-region based on the first calculating method, and calculate an elasticity value of a transverse-non-pass-region based on the second calculating method.

In an embodiment, the ultrasound diagnosis apparatus may selectively display only some of elasticity values. For example, the ultrasound diagnosis apparatus may display elasticity values calculated based on the second calculating method and may not display elasticity values calculated based on the first calculating method depending on a method of calculating an elasticity value.

FIG. 9A illustrates a result of selectively displaying only elasticity values calculated based on the second calculating method when the ultrasound diagnosis apparatus irradiates an ultrasound signal in a direction of the focus beam irradiation line 931. Referring to FIG. 9A, a partial region of a region A is determined as a shear wave-pass-region and so elasticity values thereof are not displayed.

Figure 9B:
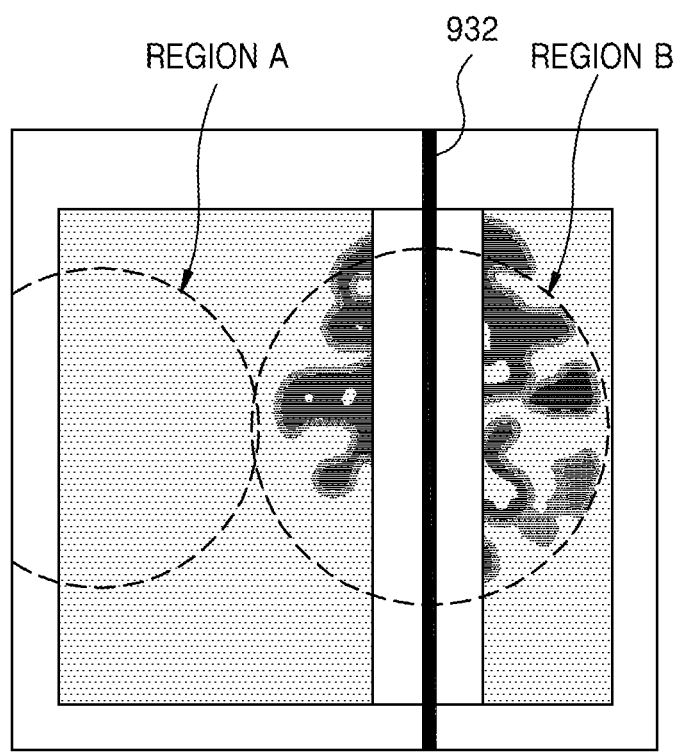

FIG. 9B illustrates a result of selectively displaying only elasticity values calculated based on the second calculating method when the ultrasound diagnosis apparatus irradiates an ultrasound signal in a direction of a focus beam irradiation line 932. Referring to FIG. 9B, a partial region of a region B is determined as a shear wave-pass-region and so elasticity values thereof are not displayed.

Figure 9C:
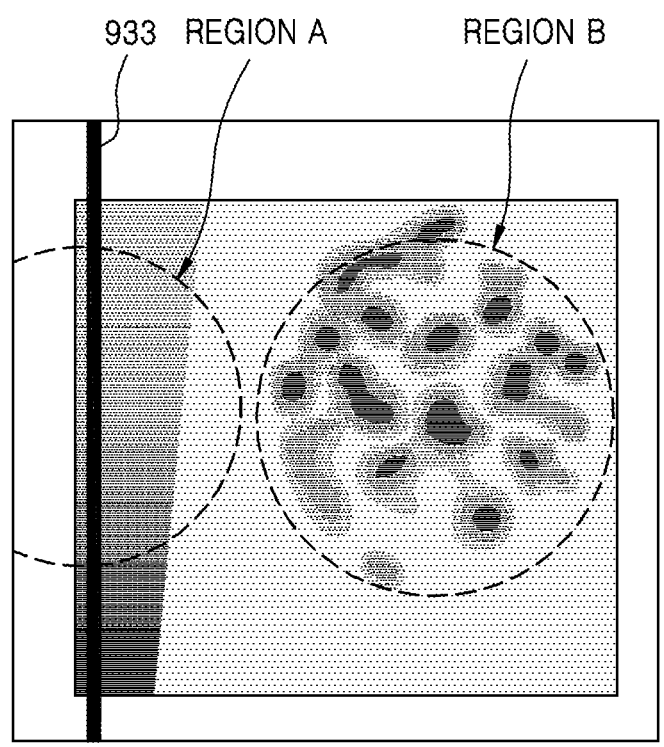

FIG. 9C illustrates a result of displaying combined elasticity values calculated based on the first calculating method and the second calculating method when the ultrasound diagnosis apparatus irradiates an ultrasound signal in a direction of a focus beam irradiation line 933. Referring to FIG. 9C, elasticity values of the entire measurement target region are displayed.

Figure 9D:
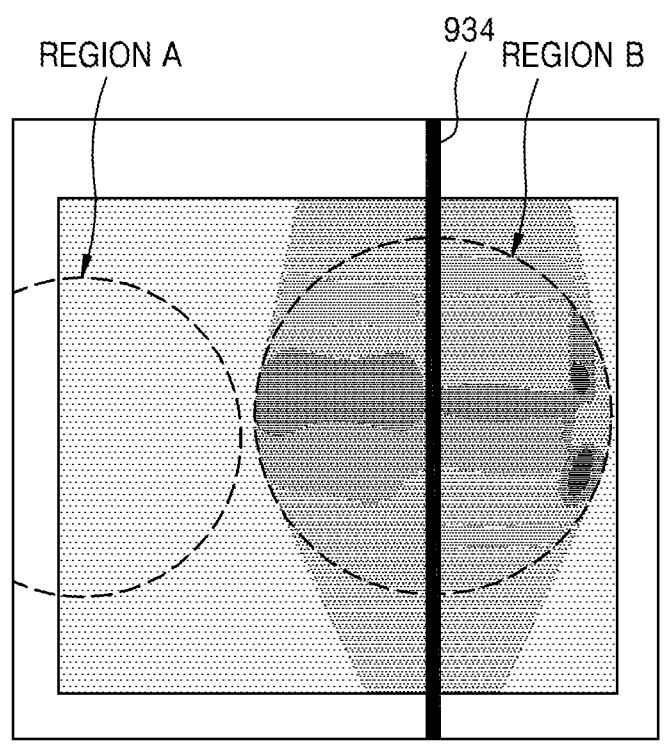

FIG. 9D illustrates a result of displaying combined elasticity values calculated based on the first calculating method and the second calculating method when the ultrasound diagnosis apparatus irradiates an ultrasound signal in a direction of a focus beam irradiation line 934. Referring to FIG. 9D, elasticity values of the entire measurement target region are displayed.

Embodiments may be implemented through non-transitory computer-readable recording media having recorded thereon computer-executable instructions and data. The instructions may be stored in the form of program codes, and when executed by a processor, may generate a predetermined program module to perform a specific operation. Furthermore, when being executed by the processor, the instructions may perform specific operations according to the embodiments.

What is claimed is:

1. An ultrasound diagnosis apparatus comprising:
a processor configured to obtain elasticity data of a measurement target region of an object, calculate elasticity values of a plurality of regions included in the measurement target region based on the elasticity data by using different calculating methods, and combine the calculated elasticity values of the plurality of regions so as to calculate a final elasticity value, wherein the different calculating methods include a first calculating method and a second calculating method; and
a display configured to display the final elasticity value, wherein the processor is further configured to:
determine an initially detected location of a shear wave displacement based on a point at which a shear wave has arrived when the shear wave has been initially observed,
set a reference value based on a distance between the initially detected location of the shear wave displacement and a focus beam irradiation line,
calculate a plurality of first distance values of the plurality of regions, respectively, based on an average distance between the plurality of regions and the focus beam irradiation line;
determine a first region as a shear wave-pass-region in which a first distance value thereof based on an average distance between the first region and the focus beam irradiation line is less than the reference value, and
determine a second region as a shear wave-non-pass-region in which a second distance value thereof based on an average distance between the second region and the focus beam irradiation line is greater than the reference value,
wherein an elasticity value of the object in the first region is calculated by the first calculating method,
wherein an elasticity value of the object in the second region is calculated by the second calculating method,
wherein the reference value is different along a direction in which the focus beam irradiation line extends, and
wherein the first calculating method is a method of estimating the elasticity value of the first region determined as the shear wave-pass-region based on the elasticity data.

2. The apparatus of claim 1, wherein the first calculating method calculates a shear wave average velocity in the shear wave-pass-region by using the initially detected location of the shear wave displacement, and predicts and calculates an elasticity value based on the shear wave average velocity.

3. The apparatus of claim 1, wherein
the processor is further configured to calculate reliability of the calculated elasticity values of the plurality of regions based on the first calculating method or the second calculating method, and
the display further displays the reliability.

4. The apparatus of claim 3, wherein the processor is further configured to set reliability of the elasticity value calculated based on the first calculating method to a preset reliability value.

5. The apparatus of claim 4, wherein the processor is further configured to control the display to selectively display only a portion of the final elasticity value based on the reliability.

6. The apparatus of claim 5, further comprising an input interface configured to receive a user input,
wherein the processor is further configured to control the display to select only a portion of the final elasticity value based on the user input, and display the selected final elasticity value and an elasticity value calculating method of the selected final elasticity value.

7. A method of operating an ultrasound diagnosis apparatus, the method comprising:
obtaining elasticity data of a measurement target region of an object;
calculating elasticity values of a plurality of regions included in the measurement target region based on the elasticity data by using different calculating methods, wherein the different calculating methods include a first calculating method and a second calculating method;
combining the calculated elasticity values of the plurality of regions to calculate a final elasticity value;
displaying the final elasticity value, wherein the plurality of regions include a first region and a second region;
determining an initially detected location of a shear wave displacement based on a point at which a shear wave has arrived when the shear wave has been initially observed;
setting a reference value based on a distance between the initially detected location of the shear wave displacement and a focus beam irradiation line;
calculating a plurality of distance values of the plurality of regions, respectively, based on an average distance between the plurality of regions and the focus beam irradiation line;
determining the first region as a shear wave-pass-region in which a first distance value thereof based on an average distance between the first region and the focus beam irradiation line is less than the reference value; and
determining the second region as a shear wave-non-pass-region in which a second distance value thereof based on an average distance between the second region and the focus beam irradiation line is greater than the reference value, wherein the calculating of the elasticity values of the plurality of regions included in the measurement target region based on the elasticity data by using the different calculating methods comprises:

calculating an elasticity value of the object in the first region by the first calculating method; and calculating an elasticity value of the object in the second region by the second calculating method, wherein the reference value is different along a direction in which the focus beam irradiation line extends, and wherein the first calculating method is a method of estimating the elasticity value of the first region determined as the shear wave-pass-region based on the elasticity data.

8. The method of claim 7, wherein the first calculating method calculates a shear wave average velocity in the shear wave-pass-region by using the initially detected location of the shear wave displacement, and predicts and calculates an elasticity value based on the shear wave average velocity.

9. The method of claim 7, further comprising:

calculating reliability of the calculated elasticity values of the plurality of regions based on the first calculating method or the second calculating method, wherein the displaying of the final elasticity value comprises displaying the final elasticity value and the reliability.

10. The method of claim 9, wherein the calculating of the reliability of the calculated elasticity values of the plurality of regions comprises setting reliability of the elasticity value calculated based on the first calculating method to a preset reliability value.

11. The method of claim 9, wherein the displaying of the final elasticity value and the reliability comprises selectively displaying only a portion of the final elasticity value based on the reliability.

12. A non-transitory computer-readable recording medium having stored therein computer program code for performing, when read and performed by a processor, a method of displaying an ultrasound image, the method comprising:

obtaining elasticity data of a measurement target region of an object;

calculating elasticity values of a plurality of regions included in the measurement target region based on the elasticity data by using different calculating methods, wherein the different calculating methods include a first calculating method and a second calculating method;

combining the calculated elasticity values of the plurality of regions to calculate a final elasticity value;

displaying the final elasticity value, wherein the plurality of regions include a first region and a second region;

determining an initially detected location of a shear wave displacement based on a point at which a shear wave has arrived when the shear wave has been initially observed;

setting a reference value based on a distance between the initially detected location of the shear wave displacement and a focus beam irradiation line;

calculating a plurality of distance values of the plurality of plurality of regions, respectively, based on an average distance between the plurality of regions and the focus beam irradiation line;

determining the first region as a shear wave-pass-region in which a first distance value thereof based on an average distance between the first region and the focus beam irradiation line is less than the reference value; and determining the second region as a shear wave-non-pass-region in which a second distance value thereof based on an average distance between the second region and the focus beam irradiation line is greater than the reference value, wherein the calculating of the elasticity values of the plurality of regions included in the measurement target region based on the elasticity data by using the different calculating methods comprises:

calculating an elasticity value of the object in the first region by the first calculating method; and calculating an elasticity value of the object in the second region by the second calculating method, wherein the reference value is different along a direction in which the focus beam irradiation line extends, and wherein the first calculating method is a method of estimating the elasticity value of the first region determined as the shear wave-pass-region based on the elasticity data.

* * * * *